US009144693B2

(12) United States Patent
Appelman et al.

(10) Patent No.: US 9,144,693 B2
(45) Date of Patent: Sep. 29, 2015

(54) IMAGE GUIDED PLAQUE ABLATION

(75) Inventors: Yolande Appelman, Amsterdam (NL); Pieter A. Doevendans, Utrecht (NL); J. Donald Knight, Excelsior, MN (US)

(73) Assignee: INTERNATIONAL CARDIO CORPORATION, Excelsior, MN (US)

( * ) Notice: Subject to any disclaimer, the term of this patent is extended or adjusted under 35 U.S.C. 154(b) by 778 days.

(21) Appl. No.: 12/145,220

(22) Filed: Jun. 24, 2008

(65) Prior Publication Data
US 2009/0048546 A1  Feb. 19, 2009

Related U.S. Application Data

(60) Provisional application No. 60/945,993, filed on Jun. 25, 2007.

(51) Int. Cl.
*A61B 5/05*  (2006.01)
*A61N 7/02*  (2006.01)

(52) U.S. Cl.
CPC .......................................... *A61N 7/02* (2013.01)

(58) Field of Classification Search
USPC .................. 600/407, 437, 471, 473, 476, 439; 601/2; 606/27
See application file for complete search history.

(56) References Cited

U.S. PATENT DOCUMENTS

| | | | |
|---|---|---|---|
| 3,985,030 A * | 10/1976 | Charlton ..................... | 73/290 V |
| 6,334,846 B1 | 1/2002 | Ishibashi et al. | |
| 6,425,867 B1 | 7/2002 | Vaezy et al. | |
| 6,542,767 B1 | 4/2003 | McNichols et al. | |
| 6,685,693 B1 | 2/2004 | Casso | |
| 2002/0193681 A1* | 12/2002 | Vitek et al. ..................... | 600/411 |
| 2003/0008920 A1* | 1/2003 | Kritchevsky ................. | 514/560 |
| 2003/0028111 A1* | 2/2003 | Vaezy et al. ................. | 600/439 |
| 2003/0036706 A1 | 2/2003 | Slayton et al. | |
| 2003/0069525 A1 | 4/2003 | Brisken et al. | |

(Continued)

FOREIGN PATENT DOCUMENTS

EP   0 627 206 A2   12/1994
EP   0 734 742 A2   10/1996

(Continued)

OTHER PUBLICATIONS

Saksena et al (Low-energy transvenous ablation of the canine atrioventricular conduction system with a suction electrode catheter, Circulation, 1987; 76:394-403, American Heart Association).*

(Continued)

*Primary Examiner* — Joel F Brutus
(74) *Attorney, Agent, or Firm* — Greenblum & Bernstein, P.L.C.

(57) ABSTRACT

A method and system for reducing vascular plaque non-invasively comprising the steps of imaging at least a portion of a mammalian body to produce an image; determining the location of at least one vascular plaque in said image; ascertaining the location of the base of said vascular plaque, said location of base being the target location; precisely determining the relative position of said target location with respect to the cardiac rhythm in the body; delivering a beam of ultrasound energy waves from a source to the relative position to elevate temperature of said target location in a pre-determined manner; monitoring the temperature of the target location; and discontinuing delivery of ultrasound energy waves when said target location achieves a pre-determined set temperature.

8 Claims, 2 Drawing Sheets

(56) References Cited

U.S. PATENT DOCUMENTS

Figure 1:
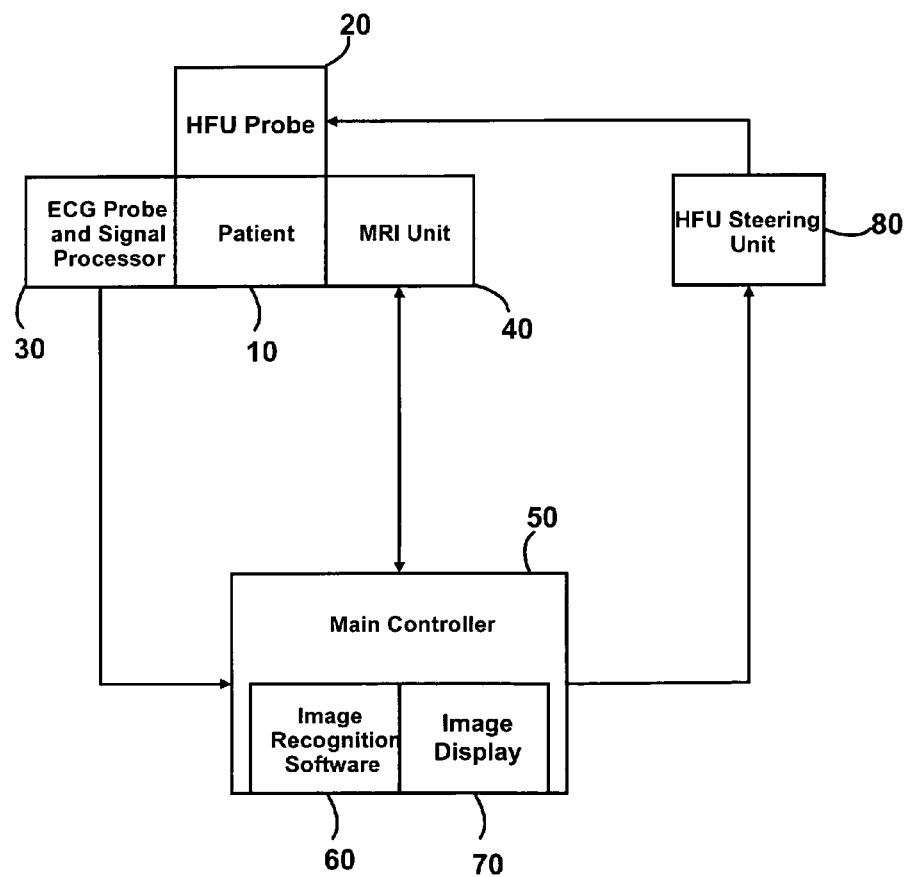

| | | | |
|---|---|---|---|
| 2003/0229283 A1* | 12/2003 | Craig et al. | 600/439 |
| 2004/0049105 A1* | 3/2004 | Crutchfield et al. | 600/407 |
| 2005/0154332 A1 | 7/2005 | Zanelli et al. | |
| 2005/0240126 A1 | 10/2005 | Foley et al. | |
| 2006/0079868 A1* | 4/2006 | Makin et al. | 606/27 |
| 2006/0116731 A1* | 6/2006 | Kramer et al. | 607/17 |
| 2006/0184163 A1* | 8/2006 | Breen et al. | 606/20 |
| 2006/0212113 A1* | 9/2006 | Shaolian et al. | 623/1.35 |
| 2007/0127789 A1* | 6/2007 | Hoppel et al. | 382/128 |
| 2007/0167705 A1* | 7/2007 | Chiang et al. | 600/407 |
| 2008/0221490 A1* | 9/2008 | Zahos | 601/2 |
| 2008/0287930 A1* | 11/2008 | Rapoport | 606/9 |

FOREIGN PATENT DOCUMENTS

| | | |
|---|---|---|
| RU | 2210409 C2 | 8/2003 |
| RU | 2004121676 A | 5/2005 |
| WO | 99/37364 A1 | 7/1999 |
| WO | 01/34018 A2 | 5/2001 |
| WO | 03/042707 A2 | 5/2003 |
| WO | 03/059168 A1 | 7/2003 |
| WO | 03/059447 A1 | 7/2003 |
| WO | 2006/129099 A1 | 12/2006 |
| WO | 2008/025667 A1 | 3/2008 |
| WO | 2008/025667 A9 | 3/2008 |
| WO | 2008/102293 A1 | 8/2008 |

OTHER PUBLICATIONS

Written opinion of the IPEA dated Jul. 15, 2009.
International Preliminary Report on Patentability dated Oct. 12, 2009.
International Search Report—mailed Nov. 7, 2008—PCT/US2008/007842.
Bernard CM te Boekhorst, et al; "ISHR World Congress Abstracts 2007: Miscellaneous", Journal of Molecular and Cellular Cardiology, vol. 42, Issue 6, Jun. 2007, 1 page.
R.J. Siegel, et al; "Ultrasonic Plaque Ablation a New Method for Recanalization of Partially or Totally Occluded Arteries", Circulation, Dec. 1988, vol. 78, No. 6, pp. 1443-1448.
Spain—Search Report dated Feb. 28, 2013; Appln. No. 200990024.
EPO Communication dated Jun. 17, 2013 Appln. No. 08 779 742.9-1652.
Maleke C. et al., "All-Ultrasound-Based System for Real-Time Monitoring and Sonication of Temperature Change and Ablation," Conference Proceedings. Annual International Conference of the IEEE Engineering in Medicine and Biology Society (IEEE Cat. No. 06CH37748); Aug. 30-Sep. 3, 2006, New York, NY, USA, pp. 164-167.
Finland Office action, dated Nov. 24, 2014 along with an English translation thereof.
Egyptian Office Action for corresponding Application No. 2009/121894 dated May 8, 2014, with a partial English translation thereof.

* cited by examiner

System Diagram

IMAGE GUIDED PLAQUE ABLATION

CROSS-REFERENCE TO RELATED APPLICATIONS

This application claims the benefit of priority to U.S. Provisional Application No. 60/945,993, filed on Jun. 25, 2007.

FIELD OF THE INVENTION

The invention relates to the field of treatment of atherosclerosis. Particularly, the invention relates to systems for reduction of vascular plaques.

BACKGROUND OF THE INVENTION

Cardiovascular disease is a leading cause of morbidity and mortality worldwide. It occurs due to the formation of plaques within the coronary arteries over time, leading to decreased blood flow to specific organs including brain and heart muscle. Under certain circumstances, this decreased blood flow can cause symptoms of transient ischemic attack, calf pain or angina. If the blockage of the arteries is more significant, it can lead to damage to the brain, legs or heart muscle itself and can be fatal.

One method of treatment of (cardio)vascular disease and avoidance of further tissue damage is through invasive elimination of the plaque. This is typically done through invasive surgery. An alternative approach is through balloon angioplasty, which involve accessing the vessels using catheterization. Arterial stents may also be placed during this procedure. When the nature of the plaque precludes treatment by angioplasty, the plaques may be bypassed by grafting new vessels around the areas of plaque during vascular or cardiac surgery procedure. In some patients, neither angioplasty nor bypass surgery is possible, such as when the advanced age or poor health of the patient precludes such treatments or when the plaque is not amenable to either therapy. In such cases, the patients must attempt to control the disease through medical management such as through the use of medication. Because the surgical treatment of arterial plaques is invasive, the treatment is associated with the risk on complications, and is not suitable for all patients, a less invasive method for reducing or eliminating plaque formations in the arteries is therefore needed.

Non-invasive methods for treatment of unwanted material in tissues and vessels, typically cardiac vessels have been suggested for instance in U.S. Pat. Nos. 5,657,760, 5,590,657, and 5,524,620. However, these methods are not suitable for the reduction of plaques, let alone in the vascular system.

Hence, there is a need for an accurate, reliable system for obviating and reducing vascular plaques with a planned and controlled treatment therapy.

SUMMARY OF THE INVENTION

This invention relates to a method and system for reducing vascular plaque.

For the purposes of this specification, the term 'cardiac rhythm' refers to all or any of the events related to the flow of blood that occur from the beginning of one heartbeat to the beginning of the next. Every single 'beat' of the heart involves three major stages: atrial systole, ventricular systole and complete cardiac diastole.

According to this invention, there is provided a method for reducing vascular plaques non-invasively comprises the following steps:

imaging at least a portion of a mammalian body to produce an image;
determining the location of at least one vascular plaque in said image;
ascertaining the location of the base of said vascular plaque, said location of base being the target location;
precisely determining the relative position of said target location with respect to the cardiac rhythm in the body;
delivering a beam of ultrasound energy waves from a source to a focal point in the relative position to elevate temperature of said target location in a pre-determined manner;
monitoring the temperature of the target location; and
discontinuing delivery of ultrasound energy waves when said target location achieves a pre-determined set temperature.

The method in accordance with this invention includes the step of displaying said image and said target location. It also includes the step of preparing a therapeutic plan for treatment of said vascular plaque. The frequency of ultrasound energy waves is adjusted to between 0.8 Hertz and about 4 Hertz. The focal point of the beam of said ultrasound energy waves is, for instance, less than about 15 mm$^3$. The intensity of focus of said ultrasound energy waves is typically adjusted to greater than about 500 W/cm$^2$. Further, the duration of the delivery of ultrasound energy waves is typically adjusted based on temperature change. Typically, the time duration for delivery of ultrasound is adjusted to between about 80 ms and about 1 second.

According to another aspect of this invention, there is provided a system for reducing vascular plaque comprising:

imaging device adapted to image at least a portion of a mammalian body;
interpreting device adapted to interpret said image to locate at least one vascular plaque and the base of said vascular plaque for determining plaque location;
monitoring device to monitor the relative position of said target location with respect to the cardiac rhythm;
at least one displaceable ultrasound delivery device adapted to deliver ultrasound energy waves of a predetermined intensity to said target location;
temperature monitoring device to monitor temperature of said target location; and
device to shut-off delivery of ultrasound energy waves when the target location achieves a predetermined set temperature.

The monitoring device is an ECG machine The ultrasound delivery device is a High Frequency Ultrasound (HFU) device. The imaging device is a Magnetic Resonance Imaging (MRI) device.

The imaging device and the interpreting device is capable of recognizing plaque in the vascular system of the imaged body and identifying the base of the plaque in the MRI images of the vessels. The HFU device is adapted to deliver HFU to the base of the plaque identified by the imaging and interpreting device as the target location. The temperature monitoring device is capable of monitoring the temperature of the tissue at the target location via the thermal images to determine when HFU delivery is complete.

The system in accordance with this invention may be used for treatment of plaques within the carotid, iliac, femoral or coronary arteries. In accordance with an additional embodiment of this invention, an ECG monitoring device is adapted to monitor cardiac rhythm during said therapeutic treatment and process signals from said monitored ECG.

The controlling device controls the timing of MRI images and the delivery of HFU according to data received from the ECG monitoring device, so that HFU delivery and MRI images are triggered at a particular point in the cardiac cycle.

The controlling device is adapted to guide the ultrasound delivery device to emit ultrasound energy waves in confirmation with:

specific angle or location of delivery;
intensity of ultrasound energy waves to be emitted; and
time duration for delivery of the ultrasound energy waves.

The aforementioned parameters depend upon the size and location of the plaque as mapped by the imaging device.

The system includes a therapeutic treatment plan for determining the parameters of the delivered ultrasound energy waves. It may include a controlling device to receive said therapeutic treatment plan from an automated control unit and/or by manual intervention.

The delivery of HFU to the base of the plaque causes the temperature of the tissue at the target location to rise. MRI monitoring of the target tissue detects the temperature increase. When the temperature increase is adequate, HFU treatment is stopped. The HFU treatment may be repeated at the same target but with an alternative angle of delivery. The HFU treatment may also be repeated at multiple target locations within the same plaques or within different plaques.

For each target, the HFU delivery is continued until an adequate amount of treatment has been delivered to lead to scarring and plaque regression.

BRIEF DESCRIPTION OF THE ACCOMPANYING DRAWINGS

Figure 2:
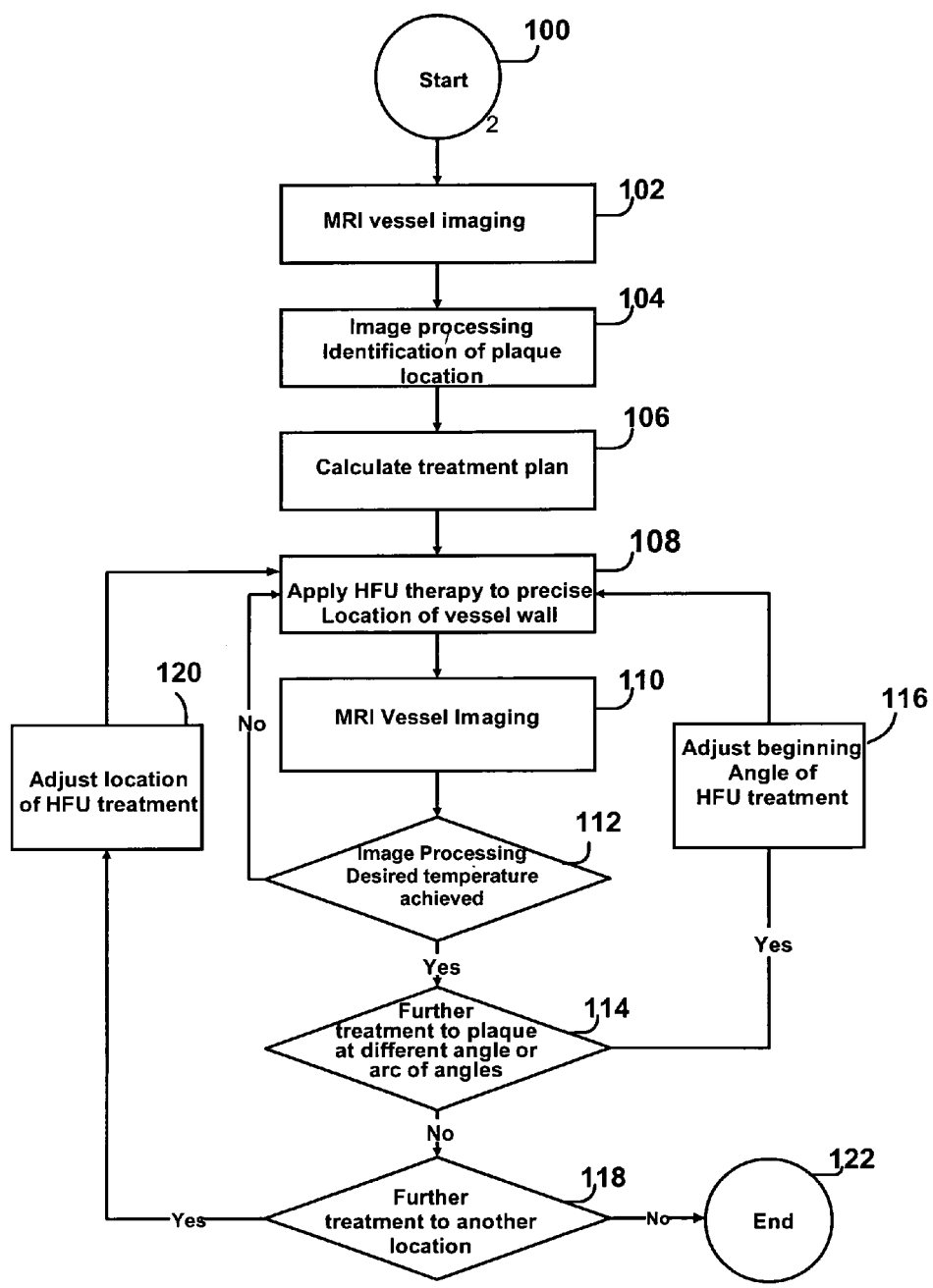

The invention will now be described in relation to the accompanying drawings, in which:

FIG. 1 illustrates the system for non-invasive reduction of vascular plaques; and FIG. 2 illustrates the method of treatment for non-invasive reduction of vascular plaques.

DETAILED DESCRIPTION OF THE ACCOMPANYING DRAWINGS

FIG. 1 illustrates the system for non-invasive reduction of vascular plaques. Treatment is delivered to the patient (10) using an ultrasound delivery device, typically through a High Frequency Ultrasound (HFU) emitting device (20). During treatment delivery, the patient (10) is monitored by both an ECG monitoring device (30) and a Magnetic Resonance Imaging (MRI) device (40). Output from the ECG monitoring device (30) and the MRI device (40) are sent to a interpreting a processing device (50) which includes image recognition device (60) and an image display device (70). The controller provides output to the HFU steering unit (80), which directs the delivery of energy by steering and controlling the HFU device (20).

During the procedure, the patient (10) is placed in a comfortable position on a treatment table where the patient must remain still. Because the procedure is non-invasive, it may be performed without any sedation and without causing the patient discomfort. The treatment table is located within the MRI device (40), so that the MRI images may be taken during the procedure to locate target lesions and to monitor the progress of the treatment. The MRI device (40) must be capable of providing images of the arteries which are sharply detailed so that the base of the plaque can be precisely identified, on the back side of the plaque at the vessel wall. An MRI device (40) which provides images with the capability to visualize tissue at a nanometer level of resolution, such as a 1.5, 3 or 7 Tesla MRI unit, may be used in embodiments of the invention to provide these precise images.

The patient (10) is also monitored by an ECG monitoring device (30) throughout the duration of the procedure. The ECG monitoring unit (30) may be a standard 12-lead ECG or may be performed using fewer leads. Like all other components used in or near the MRI device (40), the ECG monitoring device (30) must not include any ferrous material. The beating of the patient's heart results in motion of the heart as well as of all arteries as they expand with each cardiac contraction. The ECG is used to allow the system to compensate for this motion. In order to obtain useful MRI images, the taking of the MRI images is timed to correspond to the beating of the patient's heart, such that each image is taken at the same point in the cardiac cycle. For example, the MRI device can be timed to take images during diastole, the relaxation phase of the heart. Likewise the delivery of the HFU therapy is timed to the cardiac cycle using the ECG monitoring device (30). After the target location is identified using an MRI image, HFU therapy is applied to the target location. In order to ensure correct localization of the target location during treatment, the point during the cardiac cycle at which the MRI image is taken is the same as the point at which the HFU therapy is delivered. In this way, the target location identified using MRI is the same as the location to which the HFU therapy is delivered.

The ECG data is relayed to a processing device (50) throughout treatment. The processing device (50) interprets the ECG data and provides instructions to the MRI device (40) and the HFU controller (80). The processing device (50) also receives data from the MRI device (40) and includes image recognition device (60) and an image display device (70). The image recognition device (60) may be used to identify plaque within the arteries by interpreting the signal in the MRI images. Alternatively, a clinician may visually identify plaque on the image display (70) of the MRI images. In some embodiments, the image recognition device (60) identifies the plaque and the clinician verifies the identification using the image display device (70). The image recognition device (60) and/or the clinician identify the location at the base of each plaque which is the target of the HFU therapy.

After one or more target locations are identified by the processing device (50) and/or the clinician, a treatment plan is developed. A single plaque may include one target location or several target locations along the base of the plaque. In addition, an individual may have multiple plaques. In some cases, the treatment plan will include delivery of HFU to all identified plaque bases. In other cases, it may be desirable to selectively treat only some plaque bases or portions of plaque bases and leave others untreated. Therefore the treatment plan includes the decision regarding which plaque bases will be treated, and these locations become the target locations. For each target location, the ideal alignment of the HFU device (20) with the patient (10) must also be determined. This will depend upon the location of the target location as well as factors such as individual patient anatomy.

The following parameters depend upon the size and location of the plaque as mapped by the MRI device (40):

specific angle or location of delivery;
intensity of ultrasound energy waves to be emitted; and
time duration for delivery of the ultrasound energy waves.

In some cases, treatment may be delivered by a stationary HFU beam at a single angle. Alternatively, it may be preferable to deliver HFU to a target location using a stationary HFU beam at more than one treatment angle. In some cases, HFU may be delivered as the beam rotates through an arc of treatment angles. In still other cases, HFU may be delivered through multiple arcs of treatment angles. This can be by means of a multilocus transducer. The method includes the step of displacing the source of said beam. The displacement could be linear or angular. By delivering treatment using more than one treatment angle, the amount of energy delivered to tissue outside of the target location is minimized and therefore the risk of damage to other tissue may be decreased or eliminated. For each treatment angle and for each target location, a target temperature must be chosen. Therefore the treatment plan includes the details regarding which target locations are to be treated, the angle at which the HFU will be delivered, whether multiple treatment angles will be used to deliver HFU to a target location, and what the final temperature of the target location will be for each HFU delivery. The delivery of the ultrasound energy waves may be intermittent, continuous or pulsed, with the source of ultrasound delivery being displace after each pulse or after a series of pulses. The angle of delivery may be constant or changed after each pulse or a series of pulses. These determinations may be made by the processing device (50) according to guidelines in its programming, by the clinician, or by the clinician in combination with the processing device (50).

The delivery of HFU over an arc of treatment angles may be either rotational or stationary. When the treatment plan calls for the rotational delivery of HFU over an arc of angles, HFU treatment is delivered while the HFU device is actively moving. However, the rotational delivery of HFU treatment of the arteries may only be provided during a particular time window in each cardiac cycle, due to motion of the arteries. Therefore, the arc of rotational treatment may be formed by a series of miniarcs, with treatment being delivered as the HFU device rotates through a series of miniarcs with each heart beat. For example, during a first heart beat, treatment may begin at a first angle and rotate to a second angle, forming a first miniarc. With the next heart beat, treatment may resume at the second angle and rotate to a third angle, forming a second miniarc which is consecutive with the first miniarc. Treatment would thus continue rotating across the miniarcs until the miniarcs together formed the planned treatment arc. Alternatively, stationary treatment may be delivered over an arc of angles, without rotating during HFU delivery. For example, during a first heart beat, treatment may be delivered by a stationary HFU beam at a first angle. The HFU device may be adjusted slightly, such as 1 millimeter, and during a second heart beat, treatment would be delivered by the stationary HFU device at a second angle, which may be close to the first angle. The HFU device may continue to adjust to consecutive treatment angles until treatment is delivered at series of angles to form an arc of treatment angles.

Alternative is one multilocus transducer adjusted in size and format to the target vessel or an arc with more than one transducer which delivers energy in a consecutive manner.

The processing device sends instructions according to the treatment plan to the HFU controller (80), which controls the HFU delivery device (20). When the HFU delivery device (20) is inside the MRI device (40), it must not include any ferrous material. During treatment, the treatment face of the HFU delivery device (20) is in contact with the surface of the patient (10) directly or through an intermediate substance like a gel patch on the patient's neck, groin or chest, for example. When a gel patch is used, it is able to compress to correct for the distance between the patient's surface and the target location in the vessel. The use of a gel patch may therefore be appropriate for treatment plans which call for the rotational delivery of HFU therapy over a treatment arc, so that the distance between the HFU device and the target location remains constant while the HFU device rotates around the target location. The ultrasound delivery device (20) is mobile and can be precisely positioned and angled relative the patient (10) in order to direct HFU precisely to the target location. The maximum distance between the ultrasound delivery device (20) and the target location is preferably less than about 6 cm. This maximum distance may be taken into account when developing the treatment plan.

The HFU emitting ultrasound delivery device (20) delivers ultrasonic waves to the target location at the base of the plaque, causing the target location to increase in temperature. The size of the HFU focal point is preferably less than about 15 mm$^3$. This may be achieved using HFU waves at a frequency of between about 0.8 and about 4 Hertz and with an intensity of the focus of between about 500 and about 3000 W/cm$^2$. The HFU delivery device (20) delivers HFU to the target location in repeated brief intervals which are correlated to a specific point in the cardiac cycle as detected by the ECG, according to instructions from the processing device (50). The duration of each HFU delivery may be from approximately 80 milliseconds to approximately 1 second. The appropriate duration of each HFU delivery depends upon the individual patient's heart rate. The duration of each HFU delivery could be a short duration appropriate for most or all patients, regardless of the patient's heart rate. Alternatively, the duration of each HFU delivery could determined for each individual patient depending upon the measured heart rate. Finally, the duration of each HFU delivery could vary during each individual patient's treatment in response to measured heart rate.

The HFU delivery device (20) continues delivering HFU to the target location until the tissue reaches the desired temperature according to the treatment plan. In some embodiments, the maximum desired temperature of the target location is approximately 80 degrees Celsius. The temperature of the target location is determined by the processing device (50) based on images provided by the MRI device (40). In order to monitor the temperature increase, the system may periodically take MRI images during the treatment process. For example, the system may take an MRI image after each delivery of HFU treatment. Alternatively, MRI images may be taken during delivery of HFU treatment. For example, an MRI image may be taken during initial treatment, then repeated after several HFU pulses. The MRI images may then be repeated during the treatment to monitor the progress. The signal of the MRI image at the target location changes in a manner which corresponds to the temperature of the tissue. The processing device (50) includes device which can interpret the changes in the MRI image of the target location to determine the temperature of the tissue. When the desired temperature is reached, the processing device (50) instructs the HFU controller (80) to discontinue the delivery of HFU.

FIG. 2 presents a method of treatment according to embodiments of the invention. The treatment begins at the start, step 100. At step 102, MRI images are taken of the coronary vessels. The MRI images are used to identify plaque and target locations at the base of the plaque at step 104. Based on the MRI images, a treatment plan is developed at step 106 by the processing device and/or the clinician. HFU therapy is then applied to the precise location in the vessel wall at step 108 through either a stationary beam or a rotational beam. MRI imaging of the target location is performed at step 110. The MRI image is processed to determine whether the desired temperature has been achieved according to the treatment plan at step 112. If the desired temperature has not been achieved, the steps of HFU therapy 108, MRI imaging 110 and MRI image processing 112 are repeated until the desired temperature is achieved.

A determination of whether the treatment plan calls for further treatment angles or arcs of treatment angles to the target location is made at step 114. If a further treatment angle or arc of angles are planned, the starting location and beginning angle of the HFU emitting device are adjusted at step 116 and HFU therapy is applied again at step 108 to the same target location at a new angle. MRI imaging and image processing are repeated at steps 110 and 112 until the desired temperature is achieved using the new HFU device angle.

When no further treatment angles are planned for a target location, a determination is made regarding whether further treatment is planned for another target location at step 118. If no treatment is planned for other target locations, then the treatment is at an end at step 122. However, if further treatment locations are planned, then the location of the HFU device is adjusted at step 120 to deliver HFU to a new target location, and the process is repeated for the new treatment location. This is repeated until all planed target locations have been treated.

By applying HFU to the base of the plaque, the targeted tissue in the vessel wall experiences an increase in temperature. This temperature increase leads to inflammation of the tissue and later to scar formation which is sufficient to reduce or destroy the vaso vasorum, which is the vascular supply to the base of the plaque. It is believed that the loss of vascularization to the vessel wall at the base of the plaque will lead to the eventual regression of the plaque. Because the HFU is very precise, it can deliver energy to the base of the plaque without damaging the vessel wall. In this way, HFU therapy can be used to non-invasively reduce or eliminate plaque.

Embodiments of the invention non-invasively treat atherosclerotic disease using targeted ultrasound therapy, thus avoiding the risks inherent to invasive interventions. In addition, by avoiding surgery, the treatment process is easier for the patient and the clinician, can be performed more rapidly and involves less patient discomfort and a quicker and easier recovery. Furthermore, it offers a therapy option for patients who did not qualify for surgical intervention. While some embodiments of the invention are appropriate for use in the large arteries, the treatment may also be performed to reduce atherosclerosis in other locations in the body including the coronary arteries.

The image guided cardiac ablation method and system can potentially be used in the following vascular applications:

for eliminating atherosclerosis which includes removal of atherosclerotic plaques typically in a. femoralis, in a. carotis, in a. renalis, or in a coronary artery. It can also be used for eliminating thrombolysis which includes intracranial thrombosis, thrombosis in hemodialysis shunts, thrombosis in left atrial appendage (LAA), venous thrombosis, and pulmonary embolism. It can further be used for eliminating occlusion of vessels typically in medical conditions such as hemorrhage, sealing of punctures, varicosis, pseudoaneurysmata, vascular malformations in the brain, and in bloodless resection of organs, bleeding esophageal varices, and also to separate twins sharing a single placenta.

The image guided cardiac ablation method and system can potentially be extended for use in the following non-vascular applications:

in cases relating to malignancy including prostate carcinoma, breast carcinoma, hepatocellular carcinoma, renal cell carcinoma, urinary bladder carcinoma, pancreas cancer and osteosarcoma. It can also be used in other non-vascular application not relating to malignancy such as benign prostate hypertrophy, uterus fibroids, fibroadenoma (breast, liver).

Still further, the image guided cardiac ablation method and system can be used for treatment of glaucoma, pain treatment, treatment of functional disorders of the brain (epilepsy, Parkinson's disease), lithotrypsy (urinary, bile), vasectomy, synovectomy (in rheumatoid arthritis), cutaneous lesion recovery (valvular dystrophy, lymphatic drainage, skin care) and also in cases relating to atrial fibrillation (MAZE procedure).

It can also be used in Gene targeting and drug delivery applications.

While considerable emphasis has been placed herein on the specific elements of the preferred embodiment, it will be appreciated that many alterations can be made and that many modifications can be made in the preferred embodiment without departing from the principles of the invention. These and other changes in the preferred embodiment as well as other embodiments of the invention will be apparent to those skilled in the art from the disclosure herein, whereby it is to be distinctly understood that the foregoing descriptive matter is to be interpreted merely as illustrative of the invention and not as a limitation.

We claim:

1. A method for reducing vascular plaque non-invasively comprising the following steps:

imaging at least a portion of a vessel wall to produce an image;

determining the location of at least one vascular plaque in said image;

ascertaining the location of the base of said vascular plaque, said location of base being the target location;

determining a relative position of said target location with respect to the cardiac rhythm in the body;

delivering a beam of ultrasound energy waves focused onto the target location within the base of the vascular plaque in or at the vessel wall, wherein the beam of ultrasound energy waves is from a source to a focal point in the relative position to elevate temperature of said target location for a duration in a pre-determined manner, wherein the intensity of focus of said ultrasound energy waves is between about 500 $W/cm^2$ and about 3000 $W/cm^2$ and the focal point is limited to less than 15 $mm^3$;

monitoring the temperature of the target location at the focal point is performed by interpreting data from at least one of an electrocardiogram and/or images from a Magnetic Resonance Imaging (MRI) device; and discontinuing delivery of ultrasound energy waves when said target location at the focal point achieves a pre-determined set of temperature, wherein the pre-determined temperature is adjusted such that the vessel wall is not damaged by the delivery of the ultrasound energy waves.

2. The method of claim 1, further includes preparing a therapeutic plan for treatment of said vascular plaque.

3. The method of claim 1, further includes the adjusting the frequency of ultrasound energy waves between about 0.8 Hertz and about 4 Hertz.

4. The method of claim 1, further includes adjusting a duration of delivery of ultrasound energy waves between about 80 ms and 1 second.

5. A non-invasive system for reducing vascular plaque, said system comprising:

an imaging device adapted to image at least a portion of a vessel wall;

an interpreting device adapted to interpret said image to locate at least one vascular plaque and the target comprising the base of said vascular plaque for determining plaque location;

a monitoring device to monitor the relative position of said target location with respect to a cardiac rhythm of the vessel wall;

at least one displaceable or multifocal ultrasound delivery device adapted to deliver ultrasound energy waves of a predetermined intensity to said target location, wherein the intensity of focus of said ultrasound energy waves is between about 500 W/cm$^2$ and about 3000 W/cm$^2$ and a focal point at the target location is limited to less than 15 mm$^3$;

a temperature monitoring device to monitor temperature of said target location at the focal point in which the temperature device is an electrocardiogram activity and/or images from a Magnetic Resonance Imaging (MRI) device; and a shut-off delivery device for shutting off the ultrasound energy waves when the target location at the focal point achieves a pre-determined set temperature which is adjusted such that the vessel wall is not damaged by the delivery of the ultrasound energy waves.

6. The system of claim 5, wherein said system includes a controller device to control the frequency of delivery of ultrasound energy waves in the range of about 0.8 Hertz to about 4 Hertz.

7. The system of claim 5, wherein said system includes a therapeutic treatment plan for determining parameters of the delivered ultrasound energy waves.

8. The system of claim 7, wherein said system includes a therapeutic treatment plan for determining the parameters of the delivered ultrasound energy waves and includes a controller device to receive said therapeutic treatment plan from an automated control unit.

* * * * *